United States Patent
Kobayashi

(10) Patent No.: US 7,289,140 B2
(45) Date of Patent: Oct. 30, 2007

(54) VIDEO ENDOSCOPE APPARATUS

(75) Inventor: Hiroyuki Kobayashi, Saitama-ken (JP)

(73) Assignee: PENTAX Corporation, Tokyo (JP)

( * ) Notice: Subject to any disclaimer, the term of this patent is extended or adjusted under 35 U.S.C. 154(b) by 791 days.

(21) Appl. No.: 10/770,483

(22) Filed: Feb. 4, 2004

(65) Prior Publication Data
US 2004/0155957 A1    Aug. 12, 2004

(30) Foreign Application Priority Data
Feb. 7, 2003   (JP) .......................... P2003-030899

(51) Int. Cl.
  *H04N 7/18*  (2006.01)
(52) U.S. Cl. .............................. 348/68; 348/61; 348/65
(58) Field of Classification Search .................. 348/68, 348/61, 65; 600/109
See application file for complete search history.

(56) References Cited

U.S. PATENT DOCUMENTS

| | | |
|---|---|---|
| 4,930,516 A | 6/1990 | Alfano et al. |
| 5,421,337 A | 6/1995 | Richards-Kortum et al. |
| 6,099,466 A | 8/2000 | Sano et al. |
| 6,371,908 B1 | 4/2002 | Furusawa et al. |
| 6,413,207 B1 * | 7/2002 | Minami ...................... 600/109 |
| 2004/0064016 A1 | 4/2004 | Kobayashi et al. |

* cited by examiner

*Primary Examiner*—Allen Wong
(74) *Attorney, Agent, or Firm*—Greenblum & Bernstein, P.L.C.

(57) ABSTRACT

A video endoscope apparatus includes a light source unit that alternately emits white light and excitation light, a video endoscope that has a color image sensor and a light guide for guiding the light from the light source unit to the distal end, an image data acquiring section that acquires normal observation image data during emission of the white light and acquires excitation observation image data during emission of the excitation light, first and second image processors, an image generating section. The first image processor processes the normal observation image data only. The second image processor extracts reference image data from the normal observation image data, extracts fluorescent image data from the excitation observation image data and generates affected part information. The image generating section generates image data for displaying a special observation image by converting the normal observation image data based on the affected part information.

3 Claims, 3 Drawing Sheets

VIDEO ENDOSCOPE APPARATUS

BACKGROUND OF THE INVENTION

1. Field of the Invention

The present invention relates to the video endoscope apparatus to observe the inside of body cavities, such as a stomach, intestines and a bronchus.

2. Prior Art

Irradiation of light at a specific wavelength excites living tissue, which causes living tissue to emit fluorescence. Further, intensity of fluorescence emitted from abnormal living tissue that is suffering from a lesion such as a tumor or cancer is smaller than that emitted from normal living tissue. Such a phenomenon also occurs in subcutaneous living tissue under a body cavity wall.

Japanese unexamined patent publication No. P2000-023903A discloses a video endoscope apparatus that finds abnormality of subcutaneous living tissue under a body cavity wall through the use of the phenomenon. A video endoscope apparatus of such a type displays a normal observation image and a special observation image on a monitor. The normal observation image is a color image of a body cavity wall. The special observation image shows an affected area in a predetermined color (for example, red) on a monochromatic (black and white) image of a body cavity wall.

For displaying the normal observation image on the monitor, the video endoscope apparatus irradiates a body cavity wall with white light through the video endoscope and takes color pictures of the body cavity wall with using the video endoscope to generate color image data of the normal observation image. On the other hand, when the video endoscope apparatus operates to display the special observation image on the monitor, the apparatus alternatively emits visible light (reference light) within a predetermined narrow wavelength range and excitation light to excite living tissue. The video endoscope apparatus specifies positions of pixels that should be displayed as affected areas by comparing fluorescent image data that is acquired during the irradiation of the excitation light and reference image data that is acquired during the illumination of the reference light. Then the video endoscope apparatus generates color image data for displaying a monochromatic (black and white) image based on the reference image data.

Since the reference light has the narrow wavelength range, the color image data generated based on the reference image data shows a monochromatic image not a full color image. In this process, the reference image data is converted into a color image format such as RGB component image data.

After that, the video endoscope apparatus converts the color of the specified pixels in the color image data into red, thereby image data of a special observation image is generated. The generated special observation image is two color image data where the red parts exist on the monochromatic (black and white) background.

In the meantime, recently, it is required to observe an image of the body cavity wall (the background) in the special observation image as a full color image instead of a monochromatic image. In order to satisfy the requirement, the pixels representing affected areas may be displayed on the normal observation image.

However, since the reference image data and the fluorescent image data are required to specify the affected areas and the normal observation image data is required to acquire color image data according to the conventional method, the reference light, the excitation light and the white light must sequentially illuminate the body cavity within one cycle to generate one frame of the special observation image data as color image data. That is, the cycle must be divided into three periods.

As described above, since the monochromatic special observation image data is generated by comparing the reference image data and the fluorescent image data, the reference light and the excitation light sequentially illuminate the body cavity within the cycle. That is, the cycle is divided into two periods. Since the cycle for one frame is fixed, accumulation time of the image sensor for each light becomes insufficient when the cycle is divided into three periods.

Accordingly, the brightness values of the normal observation image data, the reference image data and the fluorescent image data tend to lower as a whole.

Further, the lowered brightness values cause an error in comparison of the reference image data and the fluorescent image data, which raises the problem of the disparity between the actual affected areas and the displayed affected areas.

SUMMARY OF THE INVENTION

It is therefore an object of the present invention to provide an improved video endoscope apparatus that is capable of observing a color image of the special observation image, which displays abnormal portions as a specific color over a background image, of a body cavity wall without decreasing brightness of each pixel of a normal observation image data, reference image data and fluorescence image data.

The video endoscope apparatus of the present invention adapted the following constructions to achieve the above-mentioned object.

That is, the video endoscope apparatus of the invention includes:

a light source unit that alternately emits white light covering the full range of visible region and excitation light to excite living tissue;

a video endoscope that has an insertion tube, a color image sensor and a light guide for guiding the white light and the excitation light from the light source unit to a distal end of the insertion tube;

an image data acquiring section that acquires normal observation image data captured by the color image sensor when the light source unit emits the white light and acquires excitation observation image data captured by the color image sensor when the light source section emits the excitation light;

a first image processing section that processes the normal observation image data only acquired by the image data acquiring section;

a second image processing section that extracts one color component image data as reference image data from the normal observation image data acquired by the image data acquiring section, extracts one color component image data as fluorescent image data from the excitation observation image data acquired by the image data acquiring section, calculates a difference between a brightness value of a pixel in the reference image data and a brightness value of the pixel at the same coordinate in the fluorescent image data for every pixel and generates affected part information by specifying the coordinates whose differences are larger than the predetermined threshold value;

an image generating section that generates image data for displaying a special observation image by converting the normal observation image data based on the affected part information so that the values of the pixels specified by the affected part information in the normal observation image data are converted into a predetermined level corresponding to a predetermined color; and an output section that outputs the image data generated by the image data generating section.

With this construction, the normal observation image data is received by the first and second image processing sections and the second image processing section extracts reference image data for generating the affected part information from the normal observation image data. Accordingly, it becomes unnecessary to keep a period for illuminating the reference light in a cycle for acquiring one frame of the special observation image, which can keep enough accumulation time of the white light reflected from the body cavity wall and the fluorescent light emitted from the body cavity wall on the image sensor. This prevents lowering the brightness value of each pixel in the normal observation image data output from the first image processing section and the reference image data output from the second image processing section, and reduces the errors that occur during comparison of the reference image data with the fluorescent image data for acquiring the affected part information.

DESCRIPTION OF THE ACCOMPANYING DRAWINGS

DESCRIPTION OF THE PREFERRED EMBODIMENTS

Ah embodiment of the present invention will be described hereinafter with reference to the drawings.

Figure 1:
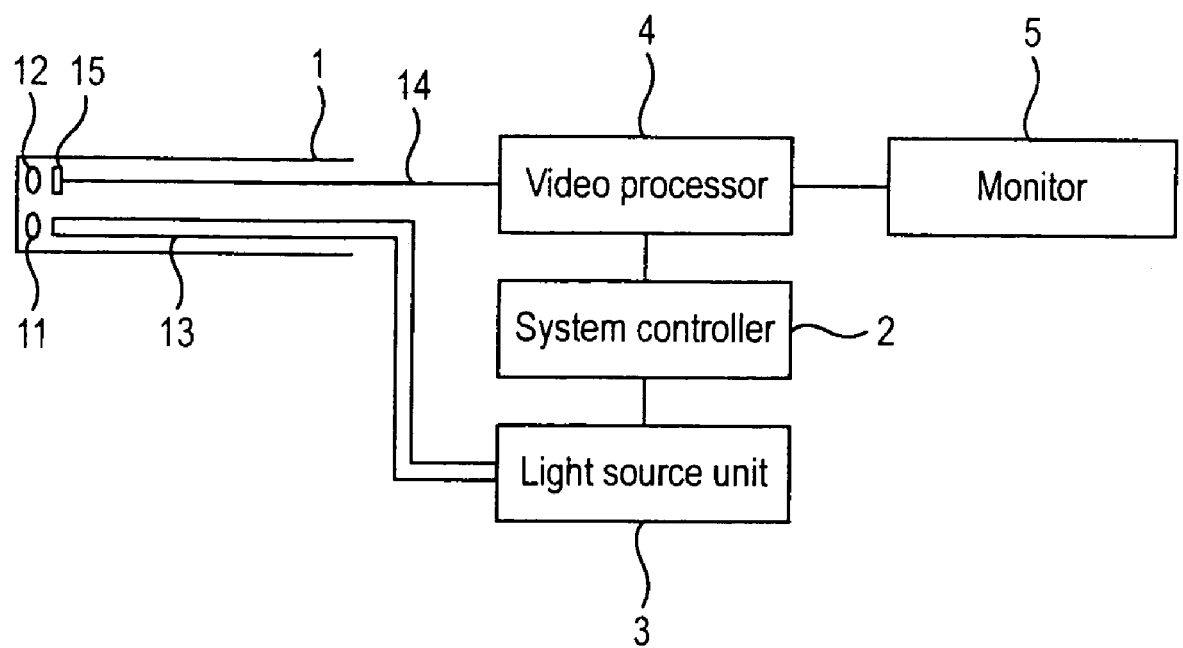
FIG. 1 is a block diagram showing a video endoscope apparatus of an embodiment according to the present invention.

FIG. 1 is a block diagram of a video endoscope apparatus of the embodiment. The video endoscope apparatus is provided with a video endoscope 1, a system controller 2, a light source unit 3, a video processor 4 and a monitor 5.

While FIG. 1 does not show the detail construction of the video endoscope 1, the video endoscope 1 has a flexible insertion tube that can be inserted into a living body. At the distal end of the flexible insertion tube of the video endoscope 1, a bending mechanism is installed. Further, angle knobs for remote-operating the bending mechanism and various kinds of switches are mounted on a proximal end of the flexible insertion tube. At least two through holes are formed on the tip surface of the flexible insertion tube, and a distribution lens 11 and an objective lens 12 are built in the through holes, respectively.

Further, a light guide 13 is led through the flexible insertion tube of the video endoscope 1. The light guide 13 is formed of a large number of flexible optical fibers that allow to transmit visible light and ultraviolet light. The distal end surface of the light guide 13 faces to the distribution lens 11 and the proximal end thereof is inserted into the light source unit 3.

Still further, a signal line 14 is Led through the flexible insertion tube of the vide endoscope 1. The proximal end of the signal line 14 is connected to a video processor 4 and the distal end thereof is connected to an image sensor 15 that is positioned at an image plane of the objective lens 12. The output signal from the image sensor 15 is received by the video processor 4 through the signal line 14.

The image sensor 15 is a single plate color area sensor that converts an image formed on an image-taking surface thereof into an image signal. Since the image sensor 15 is a general device, it will be briefly described. The image sensor 15 has a great number of photodiodes (pixels) arranged as a two-dimensional array, a charged coupled device (CCD) to transfer electrical charge accumulated on the respective photodiodes, a charge detecting device to convert the received electric charge into voltage to be output as signals, and an output circuit including a correlation double sampling circuit, etc. Further, the image sensor 15 is provided with a great number of color filters of the complementary color system arranged immediately in front of light receiving surfaces of the respective pixels. The color filters consist of four kinds of monochromatic filters that transmit-magenta (Mg) light, cyan (Cy) light, yellow (Ye) light and green (G) light, respectively. The four-color filter unit is arranged for every four-pixel group whose pixels are adjacent one another. Such an arrangement system of color filters is called a field color difference sequential system. According to the system, the CCD of the image sensor 15 is arranged so as to transmit the charge with adding charges of adjacent two pixels aligned in a predetermined direction. Therefore, the image sensor 15 sequentially outputs a signal whose level equals to the sum of brightness levels of two pixels.

Specifically, the image sensor 15 outputs two kinds of composite signals. The first composite signal alternatively represents the sum of the brightness levels of a magenta pixel (a pixel behind the filter that transmits magenta light) and a yellow pixel (a pixel behind the filter that transmits yellow light), and the sum of the brightness levels of a green pixel (a pixel behind the filter that transmits green light) and a cyan pixel (a pixel behind the filter that transmits cyan light). The second composite signal alternatively represents the sum of the brightness levels of a magenta pixel and a cyan pixel, and the sum of the brightness levels of a green pixel and a yellow pixel. Assuming that the brightness levels of the magenta, yellow, green and cyan pixels are represented by BMg, BYe, BG and BCy, the first composite signal is represented by (BMg+BYe, BG+BCy, BMg+BYe, BG+BCy, . . . ), and the second composite signal is represented by (BMg+BCy, BG+BYe, BMg+BCy, BG+BYe, . . . ).

The system controller 2 generates various reference signals and controls the light source unit 3 and the video processor 4 by the reference signals.

The system controller 2 changes an: observation mode between a normal observation mode and a special observation mode when a selector mounded on an operation panel (not shown) is switched by an operator. The system controller 2 sends a signal to represent the normal observation mode or the special observation mode to the light source unit 3 and the video processor 4 according to the current observation mode.

The light source unit 3 is provided with a lamp for emitting light that includes white light covering the full range of visible region and excitation light (ultraviolet light) to excite living tissue, a condenser lens for condensing the light emitted from the lamp onto the proximal end surface of the light guide 13, and a switching mechanism that has a shutter and filters for alternately extracting the white light and the excitation light from the light emitted from the lamp.

Receiving the signal representing the normal observation mode from the system controller 2, the light source unit 3 continuously emits the white light to be incident on the proximal end surface of the light guide 13. The incident white light is guided by the light guide 13 and diffused by the distribution lens 11 to illuminate a subject in front of the tip end of the video endoscope 1. Then, an image of the subject illuminated by the white light is formed on the image-taking surface of the image sensor 15. The image sensor 15 generates an image signal and outputs the same as an analog signal to the video processor 4. In the following description, the image data acquired when the white light is emitted from the tip end of the video endoscope 1 is referred to as normal observation image data.

Receiving the signal representing the special observation mode from the system controller 2, the light source unit 3 alternately emits the white light and the excitation light to be incident on the proximal end surface of the light guide 13. The white light and the excitation light are guided by the light guide 13 and diffused by the distribution lens 111 to alternately illuminate a subject in front of the tip end of the video endoscope 1. Then, images of the subject illuminated by the white light and by the excitation light are formed on the image-taking surface of the image sensor 15 through the objective lens 12. The image sensor 15 generates an image signal and outputs the same as an analog signal to the video processor 4. In the following description, the image data acquired when the white light is emitted from the tip end of the video endoscope 1 in the special observation mode is also referred to as the normal observation image data. Further, the image data acquired when the excitation light is emitted from the tip end of the video endoscope 1 in the special observation mode is referred to as excitation observation image data.

Receiving the signal representing the normal observation mode from the system controller 2, the video processor 4 receives the normal observation image data from the image sensor 15. The video processor 4 processes the received normal observation image data to adjust a color balance or the like, and outputs the processed normal observation image data as an analog video signal such as a PAL signal or an NTSC signal to the monitor 5. The monitor 5 displays the normal observation image based-on the input signal.

Receiving the signal representing the special observation mode from the system controller 2, the video processor 4 alternately receives the normal observation image data and the excitation observation image data from the image sensor 15. As described below, the video processor 4 generates image data to display the special observation image based on the normal observation image data and the excitation observation image data. Then the video processor 4 outputs the generated image data as an analog video signal such as a PAL signal or an NTSC signal to the monitor 5. The monitor 5 displays the special observation image-based on the input signal.

Figure 2:
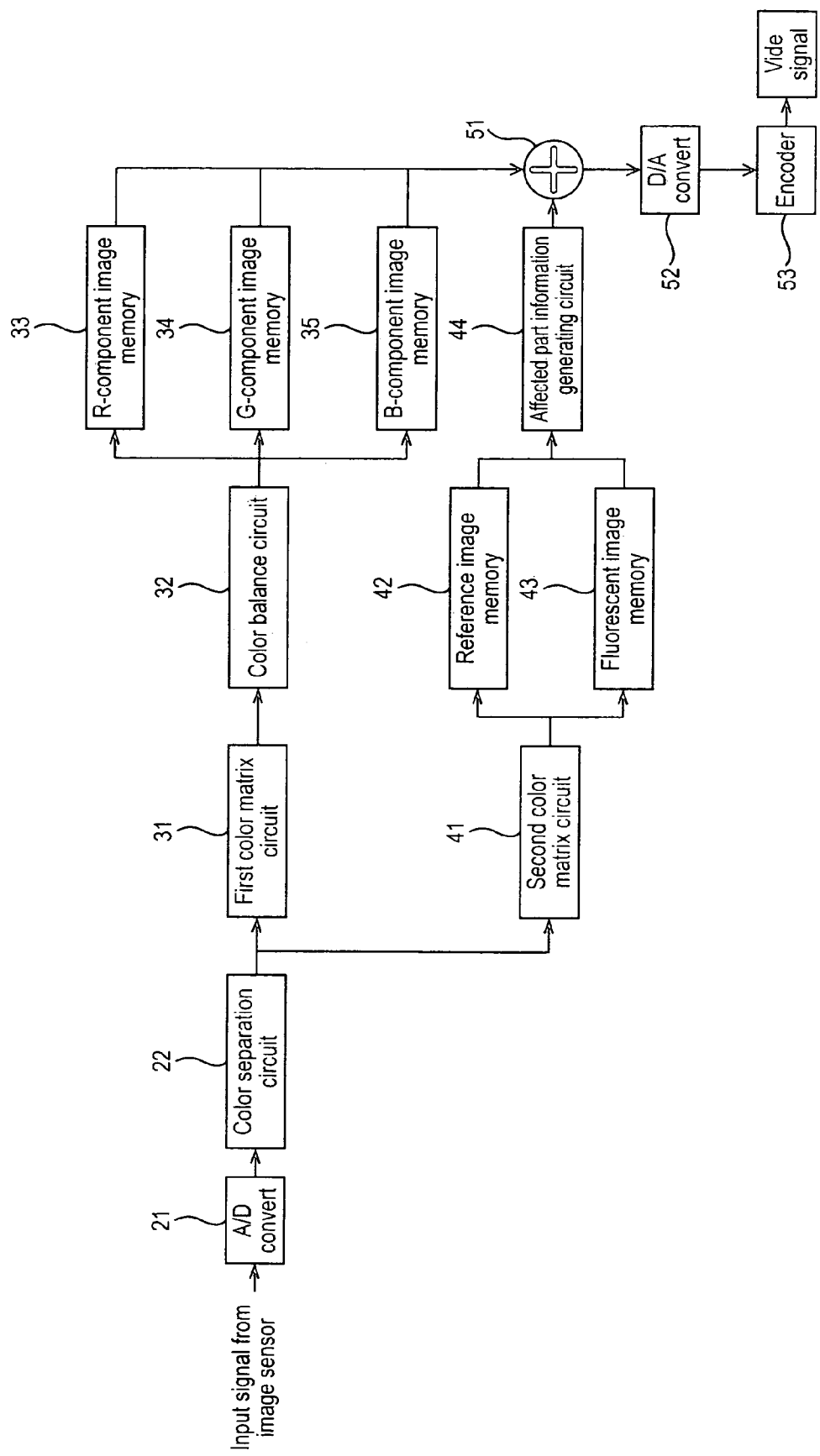
FIG. 2 is a block diagram of a video processor included in the apparatus shown in FIG. 1.

Next, the detail of the video processor 4 will be described with reference to FIG. 2 that is a block diagram of the video processor 4. The video processor 4 includes an analog/digital (A/D) converter 21, a color separation circuit 22, a first color matrix circuit 31, a color balance circuit 32, a R-component image memory 33, a G-component image memory 34, a B-component image memory 35, a second color matrix circuit 41, a reference image memory 42, a fluorescent image memory 43, an affected part information generating circuit 44, a composition circuit 51, a D/A converter 52 and an encoder 53.

Whichever observation mode is set, the image signal output from the image sensor 15 is converted by the A/D converter 21 from an analog signal format into a digital signal format. The digital signal with respect to the image data is separated into two color differential signals and one brightness signal through the well-known addition process and subtraction process in the color separation circuit 22. Since the method for generating these three signals is a general method, it will be briefly described. Logically, the two color differential signals (BMg+BYe−BG−BCy) and (BMg+BCy−BG−BYe) are generated by finding the difference of a pair of values being adjacent to each other in first and second field signals and the brightness signal (BMg+Bye+BG+BCy) is generated by finding the sum of a pair of values being adjacent to each other in the first and second field signals. In such a manner, the digital signals with respect to the image data are separated into the two color differential signals and the one brightness signal. These signals with respect to the image data output from the color separation circuit 22 are received by the composition circuit 51 through the different courses according to the observation mode.

In the normal observation mode, the two color differential signals and the one brightness signal with respect to the normal observation image data output from the color separation circuit 22 enters into the first color matrix circuit 31 and not into the second color matrix circuit 41. On the other hand, in the special observation mode, the two color differential signals and the one brightness signal with respect to the normal observation image data output from the color separation circuit 22 enter into both the first color matrix circuit 31 and the second color matrix circuit 41, and the two color differential signals and the one brightness signal with respect to the excitation observation image data output from the color separation circuit 22 enter into the second color matrix circuit 41 and not into the first color matrix circuit 31.

Hereinafter, the functions of the circuits in the video processor 4 will be described in the order of the image data processing in the normal observation mode, and then the functions in the special observation mode will be described.

In the normal observation mode, the two color differential signals and the one brightness signal with respect to the normal observation image data output from the color separation circuit 22 enter into the first color matrix circuit 31. The first color matrix circuit 31 generates a red (R) component signal, a green (G) component signal and a blue (B) component signal based on the two color differential signals and the one brightness signal. Since the method for generating these three signals is a general method, it will be briefly described. Logically, the two color differential signals and the one brightness signal are converted by the conversion determinant shown in the following formula (1) to generate three color component signals R, G and B.

$$\begin{bmatrix} R \\ G \\ B \end{bmatrix} = \alpha \begin{bmatrix} R' \\ G' \\ B' \end{bmatrix} \quad (1)$$

In the formula (1), R' denotes one color differential signal (BMg+BYe−BG−BCy) and G' denotes the other color differential signal (BMg+BCy−BG−BYe) and B' denotes the brightness signal (BMg+BYe+BG+BCy). Further, α in the formula (1) is a color matrix coefficient that can be expressed by the following formula (2), in general.

$$\alpha = \begin{bmatrix} a_{11} & a_{12} & a_{13} \\ a_{21} & a_{22} & a_{23} \\ a_{31} & a_{32} & a_{33} \end{bmatrix} \quad (2)$$

In the first color matrix circuit 31 of the embodiment, the color matrix coefficient α is determined as the following formula (3) so as to generate the suitable three color component signals R, G and B based on the two color differential signals and the one brightness signal, for example.

$$\alpha = \begin{bmatrix} 2.16 & 0.52 & -0.24 \\ -0.48 & 0.72 & -0.68 \\ -0.24 & 0.68 & 1.32 \end{bmatrix} \quad (3)$$

The color balance circuit 32 performs a color balance process on the normal observation image data output from the first color matrix circuit 31 as the three color component signals R, G and B. The color balance process is a general process to adjust the color balance of the color image displayed by the normal observation image data.

The R-, G- and B-component image memories 33, 34 and 35 temporally store the R, G and B component signals, respectively when the color balance circuit 32 outputs the normal observation image data as the R, G and B component signals. The image data of the three color components R, G and B stored in the R-, G- and B-component image memories 33, 34 and 35 are simultaneously output as the three color component signals R, G and B that enter into the D/A converter 52 through the composition circuit 51. The composition circuit 51 does not work in the normal observation mode and works in the special observation mode.

When the three color component signals that constitute the normal observation image data enter into the D/A converter 52, the D/A converter 52 converts the digital signal into the analog signal that enters into the encoder 53. The encoder 53 converts the three color component signals R, G and B with respect to the normal observation image data into a video signal such as a PAL signal and an NTSC signal. The encoder 53 outputs the video signal to the monitor 5. The monitor 5 displays the normal observation image based on the input video signal.

In the special observation mode, the normal observation image data and the excitation observation image data alternately enter into the second color matrix circuit 41, and the normal observation image data also enters into the first color matrix circuit 31. The two color differential signals and the one brightness signal with respect to the normal observation image data input to the first color matrix circuit 31 are processed by the first color matrix circuit 31 and the color component signals R, G and B output from first color matrix circuit 31 are processed by the color balance circuit 32 and are received by the composition circuit 51 through the R-, G- and B-component image memories 33, 34 and 35 as in the case of the normal observation image data in the normal observation mode.

On the other hand, the second color matrix circuit 41 converts the two color differential signals and the one brightness signal with respect to the normal observation image data into the three color component signals R, G and B. The second color matrix circuit 41 also converts the two color differential signals and the one brightness signal with respect to the excitation observation image data into the three color component signals R, G and B. However, the calculation process of the second color matrix circuit 41 for the normal observation image data is different from that for the excitation observation image data.

The second color matrix circuit 41 performs the calculation process on the two color differential signals and the one brightness signal with respect to the normal observation image data with using the conversion determinant of the formula (1) in which the matrix coefficient α is set as the following formula (4), for example.

$$\alpha = \begin{bmatrix} 1 & 0 & 0 \\ 0 & 0 & 0 \\ 0 & 0 & 0 \end{bmatrix} \quad (4)$$

With this process, only the R component signal among the three color component signal R, G and B output from the second color matrix circuit 41 has a value larger than 0 for the normal observation image data. Therefore, the second color matrix circuit 41 outputs only the R component signal when the normal observation image data is processed. The output R component signal is stored in the reference image memory 42. In the following description, the image data carried by the R component signal with respect to the normal observation image data is referred to as reference image data.

Further, the second color matrix circuit 41 performs the calculation process on the two color differential signals and the one brightness signal with respect to the excitation observation image data with using the conversion determinant of the formula (1) in which the matrix coefficient α is set as the following formula (5), for example.

$$\alpha = \begin{bmatrix} 0 & 0 & 0 \\ 0 & 1 & 0 \\ 0 & 0 & 0 \end{bmatrix} \quad (5)$$

With this process., only the G component signal among the three color component signals R, G and B output from the second color matrix circuit 41 has a value larger than 0 for the excitation observation image data. Therefore, the second color matrix circuit 41 outputs only the G component signal when the excitation observation image data is processed. The output G component signal is stored in the fluorescent image memory 43. In the following description, the image data carried by the G component signal with respect to the excitation observation image data is referred to as fluorescent image data.

The reference image data stored in the reference image memory 42 and the fluorescent image data stored in the fluorescent image memory 43 are simultaneously retrieved and enter into the affected part information generating circuit 44.

The affected part information generating circuit 44 specifies the pixels that should be displayed as affected parts in the image to acquire the information about the positions of the pixels (the affected part information). Acquiring the reference image data and the fluorescent image data for one frame, the affected part information generating circuit 44 extracts the maximum brightness value and the minimum brightness value from each of the reference image data and the fluorescent image data. Then, the affected part information generating circuit 44 standardizes the reference image data and the fluorescent image data based on the extracted maximum and minimum brightness values so that the gradation range and the level of the reference image data are coincident with that of the fluorescent image data. Next, the affected part information generating circuit 44 calculates difference between a brightness value of a pixel in the reference image data and a brightness value of the pixel at the same coordinate in the fluorescent image data (difference calculated by subtracting a pixel value of the fluorescent image data from a pixel value of the reference image data) for each coordinate. Then, the affected part information generating circuit 44 specifies the coordinates whose differences are larger than the predetermined threshold value from all coordinates. The affected part information generating circuit 44 outputs the acquired affected area information to the composition circuit 51.

The composition circuit 51 composes the normal observation image data retrieved from the R-, G- and B-component image memories 33, 34 and 35 and the affected part information output from the affected part information generating circuit 44. Specifically, the composition circuit 51 converts the values of the pixels in the normal observation image data whose coordinate is indicated by the affected-part information so that the pixels are displayed as green pixels (the gradation values of the pixels satisfy (R, G, B)=(0, 255, 0)), for example. The composition circuit 51 outputs the image data acquired by composing the normal observation image data with the affected part information to the D/A converter 52 as the image data to display the special observation image in the format of the three color component signals R, G and B.

The D/A converter 52 converts the digital special observation image data into the format of the analog signal and the converted image data enters into the encoder 53. The encoder 53 converts the three color component signals R, G and B with respect to the special observation image data into a video signal such as a PAL signal and an NTSC signal. The video signal is output from the encoder 53 to the monitor 5. The monitor 5 displays the special observation image according to the input video signal.

Since the video endoscope apparatus of the embodiment has the above-described construction, an operator of the video endoscope apparatus can observe an inside of body cavity of a subject according to the following procedure.

First, the operator inserts the distal end of the video endoscope 1 into the body cavity of the subject and sets the observation mode in the normal observation mode by operating a switch on an operation panel (not shown). Then, the white light is continuously emitted from the tip end of the video endoscope 1 and the image sensor 15 captures an image of the body cavity wall illuminated by the white light.

The color separation circuit 22 separates the normal observation image data acquired by the capturing into two color differential signals and one brightness signal. The first color matrix circuit 31 converts the separated signals into three color component signals R, G and B, and the color balance circuit 32 performs the color balancing process on the separated signals. The color component signals are stored in the R-, G- and B-component image memories 33, 34 and 35, respectively, to adjust their timings. The encoder 53 converts the color component signals retrieved from the memories 33, 34 and 35 into the video signal and outputs the video signal to the monitor 5. Accordingly, the monitor 5 displays the color normal observation image showing the area to which the tip end of the video endoscope 1 faces. The operator can observe the condition of the body cavity wall with watching the normal observation image.

Further, the operator uses the special observation image to observes the part of the body cavity wall selected through the observation of the normal observation image. Specifically, the operator sets the observation mode in the special observation mode by operating the switch on the operation panel (not shown). Then, the white light and the excitation-light are alternately emitted from the tip end of the video endoscope 1 and the image sensor 15 alternately captures an image of the body cavity wall illuminated by the white light and an image of the body cavity wall that emits fluorescence. The color separation circuit 22 separates-each of the normal observation image data and the excitation observation image data acquired by the capturing into two color differential signals and one brightness signal. The first color matrix circuit 31 converts the two color differential signals and the one brightness signal with respect to the normal observation image data into three color component signals R, G and B, and the color balance circuit 43 performs the color balancing process on the color component signals. The color component signals are stored in the R-, G- and B-component image memories 33, 34 and 35, respectively. On the other hand, the second color matrix circuit 41 extracts the reference image data from the two color differential signals and the one brightness signal with respect to the normal observation, image data. The reference image memory 42 stores the extracted reference image data. The second color matrix circuit 41 extracts the fluorescent image data from the two color differential signals and the one brightness signal with respect to the excitation observation image data. The fluorescent image memory 43 stores the extracted fluorescent image data.

The affected part information generating circuit 44 generates the affected part information by comparing the reference image data and the fluorescent image data retrieved from the reference image memory 42 and the fluorescent image memory 43, respectively. Then, the composition circuit 51 composes the R, G and B color component signals retrieved from the R-, G- and B-component image memories 33, 34 and 35 with the affected part information to generate special-observation image data for displaying the special observation image. The special observation image data is converted into an analog signal by the D/A converter 52 and the analog signal is converted into a video signal by the encoder 53. The monitor 5 displays the special observation image of the area to which the tip end of the video endoscope 1 faces as a color image.

The operator can recognize contour and irregularity of the body cavity wall by the RGB color image in the special observation image and can recognize parts that have high risk to be suffering from a lesion such as a tumor or cancer by the maculate and/or block green parts, which correspond to the living tissue emitting relatively weak fluorescence, in the special observation image.

As described above, the video endoscope apparatus of the embodiment is provided with a first channel for processing the normal observation image data (the first color matrix circuit 31, the color balance circuit 32 and the R-, G- and B-component image memories 33, 34 and 35; corresponding to the first image processing section) and a second channel for generating affected part information (the second color matrix circuit 41, the reference image memory 42, the fluorescent image memory 43 and the affected part information generating circuit 44; corresponding to the second image processing section). In the special observation mode, the normal observation image data is supplied to the both channels and the second channel extracts the reference image data, which is used for generating the affected part information, from the normal observation image data. Therefore, it becomes unnecessary to keep a period for illuminating the reference light in a cycle for acquiring one frame of the special observation image, which can keep enough accumulation time of the white light reflected from the body cavity wall and the fluorescent light emitted from the body cavity wall on the image sensor 15. This prevents lowering the brightness value of each pixel in the normal observation image data and the reference image data as a whole, and reduces the errors that occur during comparison of the reference image data with the fluorescent image data for acquiring the affected part information.

Figure 3:
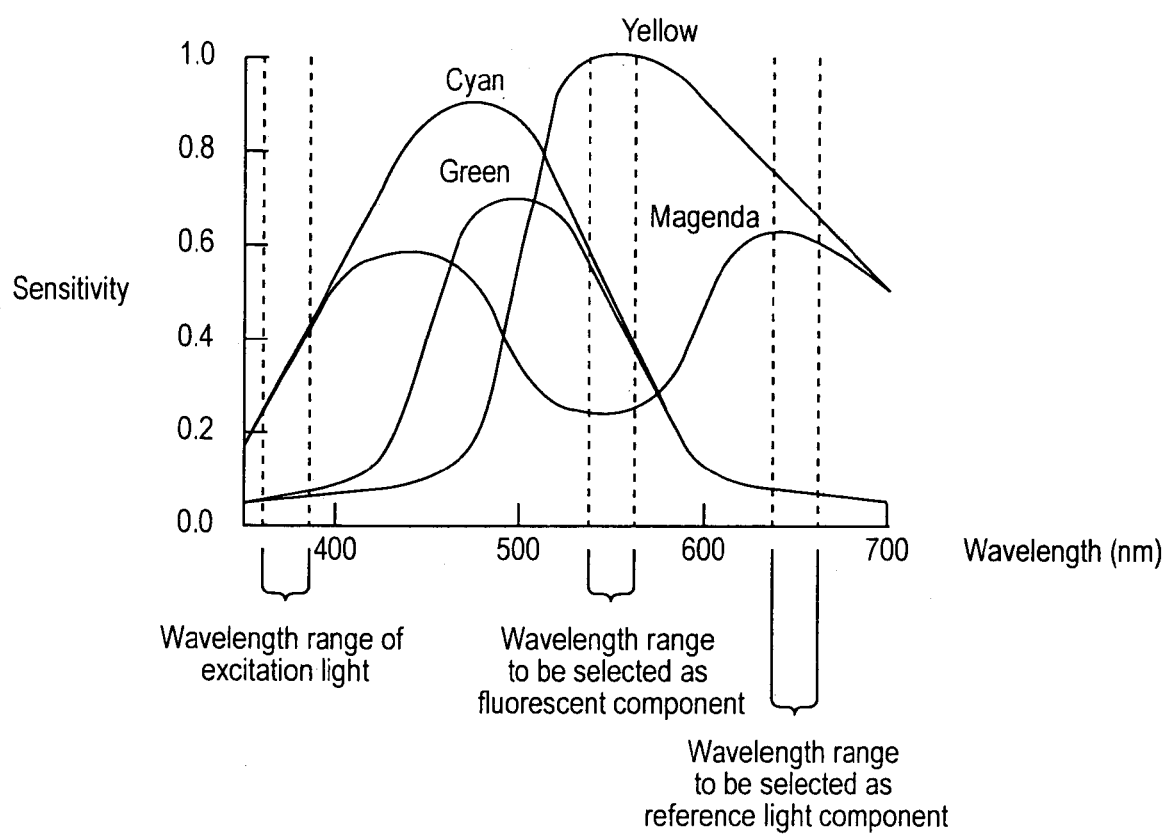
FIG. 3 is a graph showing spectral sensitivity characteristic of an image sensor as a color area sensor.

Further, according to the embodiment, since the image sensor 15 built in the video endoscope is a color area sensor, it can sense the excitation light that has a wavelength range of several nanometers containing 365 nm as shown in FIG. 3. FIG. 3 shows spectral sensitivity characteristics of the color area sensor. Therefore, if the two color differential signals and one brightness signal are converted into the three color component signals R, G and B through the calculation using a normal color matrix coefficient α as shown in the above formula (4), an alias owing to the excitation light is mixed into the color component signals, which disturbs proper reproduction of the fluorescent image data transmitted by the green component signal.

On the other hand, since the value of each element of the color matrix coefficient α is appropriately set in the embodiment, the G component signal has the fluorescence component only, which can eliminate the effect of the alias owing to the excitation light from the fluorescent image data. As a result, it is unnecessary to arrange a band-pass filter to remove the excitation light immediately in front of the image-taking surface of the image sensor 15.

Although the embodiment discloses the video endoscope apparatus that is a combination of the system controller 2, the light source unit 3 and the video processor 4 that are specially designed for the present invention with the video endoscope 1, the scope of the present invention is not limited to the embodiment. For example, a specially designed device for the invention including the system controller 2, the light source unit 3 and the video processor 4 maybe added to an ordinary video endoscope apparatus that has its original system controller, light source unit and video processor. In such a case, the added system controller 2 does not change the observation mode and always sets the condition in a mode corresponding to the special observation mode. Further, an optical fiber to guide the white light and the excitation light is attached to the added light source unit 3. The optical fiber is inserted through a forceps channel such that the tip end of the optical fiber is projected from the distal end surface of the endoscope under service conditions. Still further, the added video processor 4 receives image data output from the ordinary endoscope apparatus and executes the processes similar to the processes by the A/D converter 21 and the downstream circuits of the embodiment. In such a case, the signal output from the added video processor 4 may be received by a monitor that is connected with the ordinary endoscope apparatus or by another monitor. In the former case, a switching device is required to switch between the video signal from the original video processor of the ordinary endoscope apparatus and the video signal from the added video processor 4. In the latter case, an operator can use two monitors during observation.

As described above, the present invention enables a user to observe a color image of a body cavity wall in the special observation image without lowering brightness value of each pixel in the normal observation image data, the reference image data and the fluorescent image data. Further, the effect of the alias owing to the excitation light can be eliminated from the fluorescent image data without arranging a band-pass fitter to remove the excitation light immediately in front of the image-taking surface of the image sensor The present disclosure relates to the subject matter contained in Japanese Patent Application No. 2003-030899, filed on Feb. 7, 2003, which is expressly incorporated herein by reference in its entirety.

What is claimed is:

1. A video endoscope apparatus comprising:
  a light source unit that alternately emits white light covering the full range of visible region and excitation light to excite living tissue;
  a video endoscope that has an insertion tube, a color image sensor and a light guide for guiding the white light and the excitation light from said light source unit to a distal end of said insertion tube;
  an image data acquiring section that acquires normal observation image data captured by said color image sensor when said light source unit emits the white light and acquires excitation observation image data captured by said color image sensor when said light source section emits the excitation light;
  a first image processing section that processes said normal observation image data only acquired by said image data acquiring section;
  a second image processing section that extracts one color component image data as reference image data from said normal observation image data acquired by said image data acquiring section, extracts one color component image data as fluorescent image data from said excitation observation image data acquired by said image data acquiring section, calculates a difference between a brightness value of a pixel in said reference image data and a brightness value of the pixel at the same coordinate in said fluorescent image data for every pixel and generates affected part information by specifying the coordinates whose differences are larger than the predetermined threshold value;

an image data generating section that generates image data for displaying a special observation image by converting said normal observation image data based on said affected part information so that the values of the pixels specified by said affected part information in said normal observation image data are converted into a predetermined level corresponding to a predetermined color; and an output section that outputs said image data generated by said image data generating section.

2. The video endoscope apparatus according to claim 1, wherein said second image processing section generates three color component signals R, G and B by a calculation using a conversion determinant shown in the following formula:

$$\begin{bmatrix} R \\ G \\ B \end{bmatrix} = \begin{bmatrix} 1 & 0 & 0 \\ 0 & 0 & 0 \\ 0 & 0 & 0 \end{bmatrix} \begin{bmatrix} R' \\ G' \\ B' \end{bmatrix}$$

where
 R' is one color differential signal,
 G' is the other color differential signal, and
 B' is a brightness signal.

3. The video endoscope apparatus according to claim 1, wherein said second image processing section generates three color component signals R, G and B by a calculation using a conversion determinant shown in the following formula:

$$\begin{bmatrix} R \\ G \\ B \end{bmatrix} = \begin{bmatrix} 0 & 0 & 0 \\ 0 & 1 & 0 \\ 0 & 0 & 0 \end{bmatrix} \begin{bmatrix} R' \\ G' \\ B' \end{bmatrix}$$

where
 R' is one color differential signal,
 G' is the other color differential signal, and
 B' is a brightness signal.

* * * * *